US00PP11029P

United States Patent [19]

Sallin

[11] Patent Number: Plant 11,029

[45] Date of Patent: Aug. 10, 1999

[54] SOUTHERN MAGNOLIA TREE NAMED 'CLTF1'

[76] Inventor: Michel Sallin, 7836 Cherry Lake Rd., Groveland, Fla. 34736

[21] Appl. No.: 09/003,214

[22] Filed: Jan. 6, 1998

[51] Int. Cl.[6] ..... A01H 5/00

[52] U.S. Cl. ..... Plt./223

[58] Field of Search ..... Plt./223

[56] References Cited

U.S. PATENT DOCUMENTS

P.P. 2,015 1/1961 Rensselaer ..... Plt./223

*Primary Examiner*—Howard J. Locker
*Assistant Examiner*—Kent L. Bell

[57] ABSTRACT

A new Southern magnolia of the grandiflora variety distinguished by its rapid growth rate and an abundant branch and foliage development which maintains a very full canopy. The full canopy is supported by strong branching angles. The shiny new leaves are contrasted with a copper-brown pubescence on the under surface. This new magnolia is further distinguished by its magenta colored receptacle on the flowers and profuse production of large white flowers which are extremely fragrant, more than those of the straight species. Straight species are sexually propagated from seeds or originate in the wild.

4 Drawing Sheets

BACKGROUND OF THE NEW PLANT

My new variety of *Magnolia grandiflora,* commonly called Southern magnolia, was discovered by me in 1987. I have given my plant the variety name 'CLTF1'.

Southern Magnolia from seed are extremely variable and often unpredictable in growth shapes, growth rates, leaf characteristics, flowering characteristics and branching structure.

The parent tree of the new variety was discovered from a block of 350 Southern magnolia trees that ranged in height from 8–12 feet with a spread of 5–6 feet. These trees were grown in my nursery in native soil under normal cultivation located in Groveland, Fla. The original trees were produced from seeds from open pollination. My attention was drawn to the new plant due to it having a superior growth habit, structure, flower and foliage characteristics.

I have reproduced this new variety of Southern magnolia tree by means of cuttings at my nursery in Groveland, Fla., successfully since 1988. From the nine years of successive generations I was able to thereby determine that the novel and distinctive features of my new Southern magnolia variety remain true from generation to generation and appear to be firmly fixed.

SUMMARY OF THE NEW PLANT

The major distinguishing characteristics that set this variety apart from other Southern magnolia cultivars and seedlings are:

1. dense well branched canopy.
2. copper-brown pubescence on the leaves under surface.
3. large fragrant flowers that exhibit a unique magenta color on the receptacle.
4. dominant central leader with strong branching angles.

BRIEF DESCRIPTION OF THE DRAWINGS

The accompanying color photographs depict the distinguishing characteristics of my new Southern magnolia variety.

BOTANICAL DESCRIPTION OF THE NEW PLANT

Figure 1:
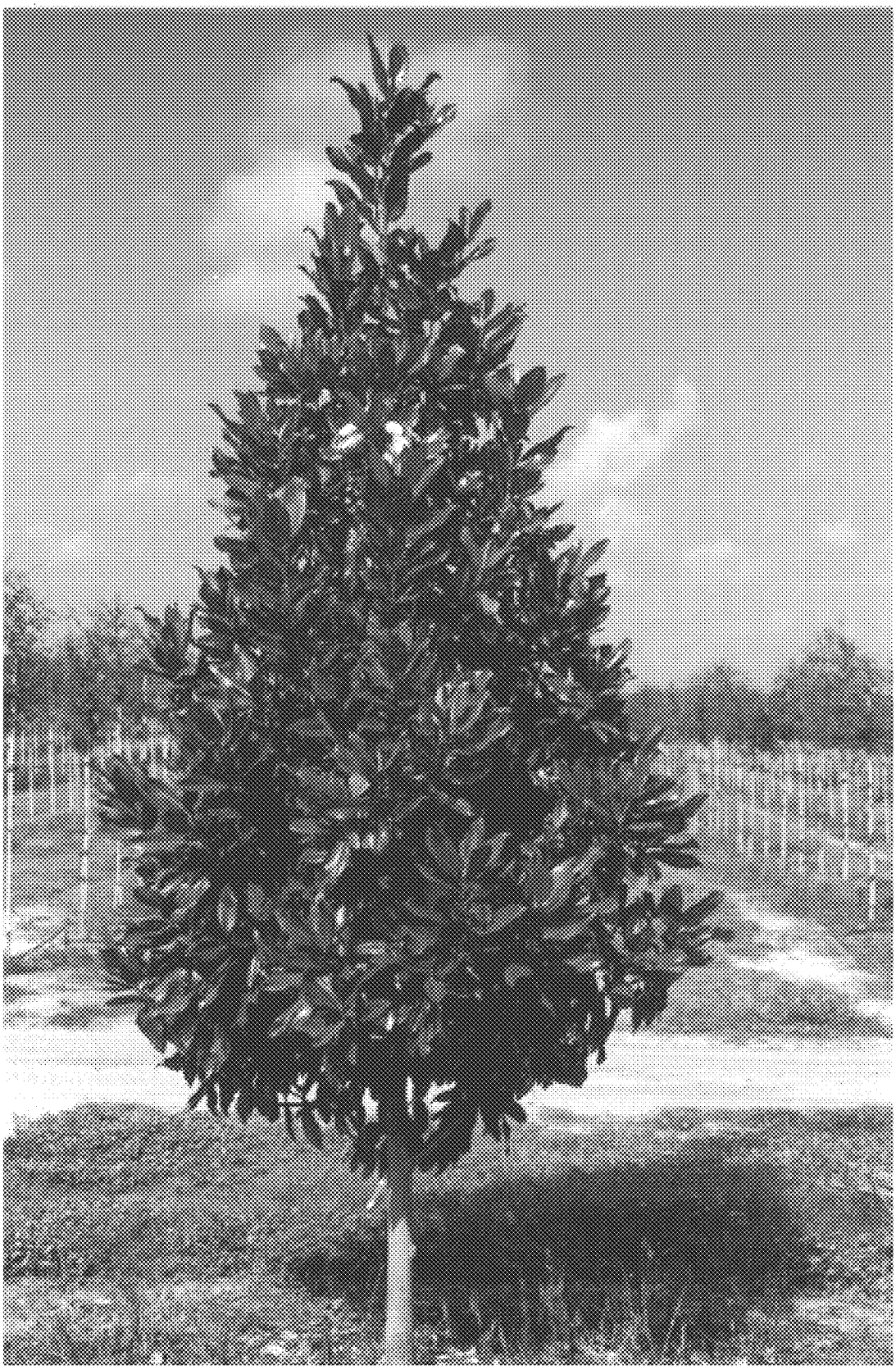
FIG. 1 illustrates the new variety in a nursery row that is 5 years old and stands 10–12 feet tall with a 5–6 feet spread and 2¾ inch caliper. This illustrates the upright central leader and well branched canopy. Photograph taken during spring flush.
Figure 2:
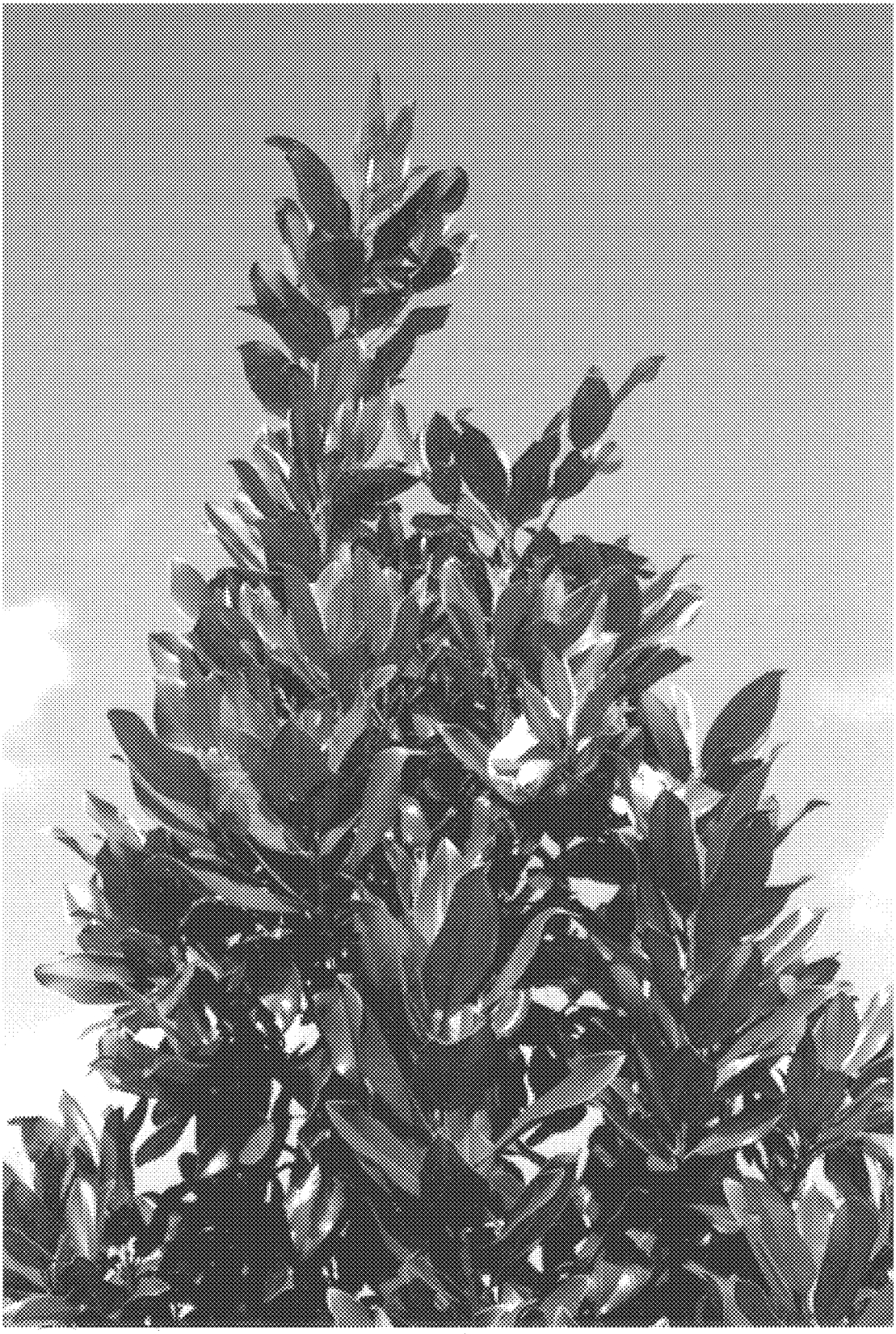
FIG. 2 shows a close-up of the leaves in FIG. 1 showing the copper-brown pubescence on the under surface and shiny green upper surface.

The following is a detailed description of my new variety of Southern magnolia based upon observations from a tree growing at Cherry Lake Tree Farm for the past 10 years. All color terminology is in accordance with The Royal Horticultural Society Colour Chart, published by The Royal Horticultural Society of London.

Origin: Seedling.

Parentage: Unknown. The seedling originated in a group of seedling grown Southern magnolias, the original trees were produced from seeds from open pollination of a number of Southern magnolias.

Classification:

*Botanic.—Magnolia grandiflora.*

*Commercial.*—Southern magnolia.

Propagation: Asexual reproduction using terminal 6–8 inch semi-hardwood cuttings with 5 leaves, wound on one side, quick dipped in 10,000 ppm KIBA for 3 seconds. Soil consisted of pine bark and peat amended with lime. Cuttings placed under intermittent mist will root in 12–16 weeks. Holds to distinguishing characteristics through succeeding propagation.

Locality where grown and observed: Groveland, Fla.

Tree: Tall evergreen tree. Pyramidal growth habit having a straight and strong central trunk. Trunk color is typical for species. Naturally maintains a dense habit because of its abundant scaffold branch development.

Height: In a period of six years from a rooted cutting, the plant reaches a height of 16 to 18 feet, with a spread of 5 to 6 feet and trunk caliper of 4 inches.

Vigor and uniformity: Vigorous, being faster growing than other popular Southern magnolia cultivars. My cultivar has at least two major flushes each year. It is common for my Southern magnolia to elongate 18 to 24 inches during the spring flush that begins in March and goes to May. Not only does my new tree grow faster than other Southern magnolia cultivars, there are less culls. It is typical for me to repot into larger pots 90 percent of this new variety's 3 gallon crop, compared to 70 percent of other Southern magnolia cultivars that are typically repotted into larger pots.

Branching: From cuttings this plant begins branching early. It's common to have lateral branching on a one year plant beginning less than one foot off the ground. As the tree ages, it maintains a dense framework of branches and leaves, producing a central leader through the canopy with strong lateral branching. These lateral branches ascend at an angle of about 55 degrees from the leader, making a very strong branch attachment.

Figure 3:
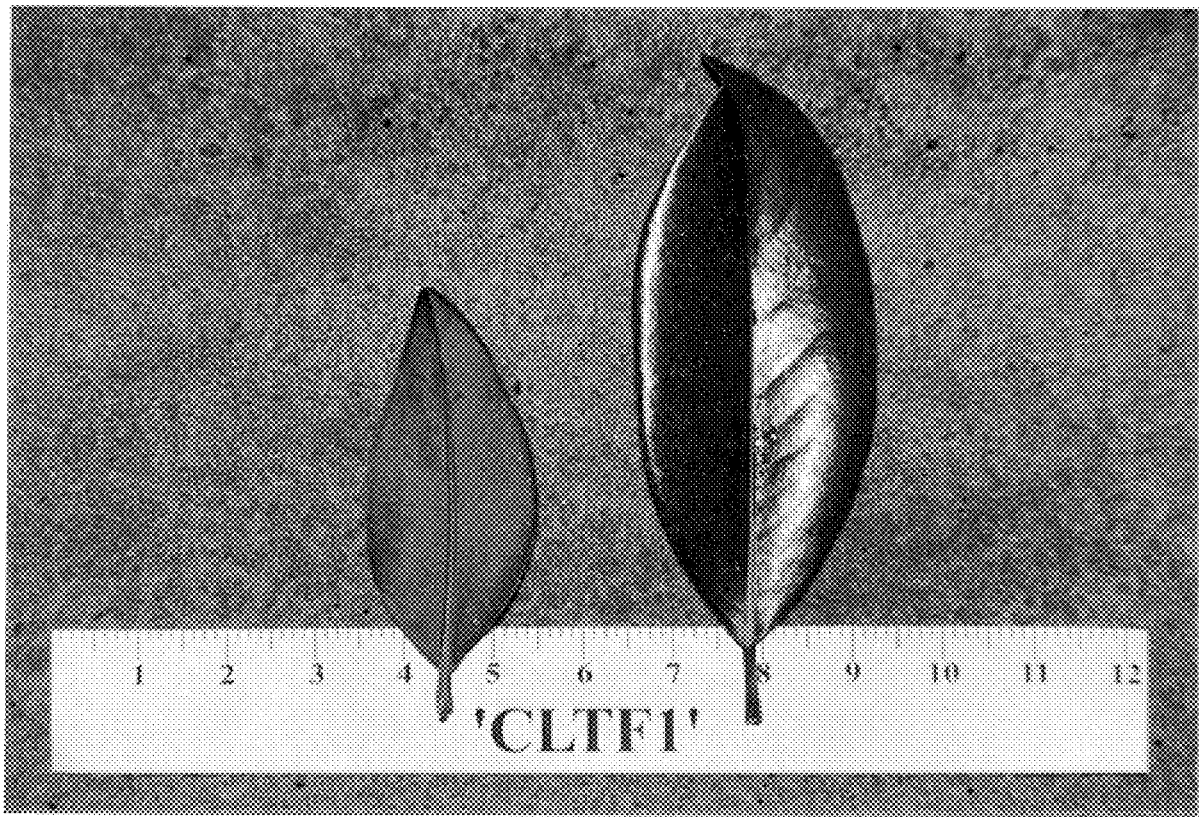
FIG. 3 shows the bottom of a newly expanding leaf (left side) and top surfaces of a fully expanded leaf(right side). Photograph taken in December.
Figure 4:
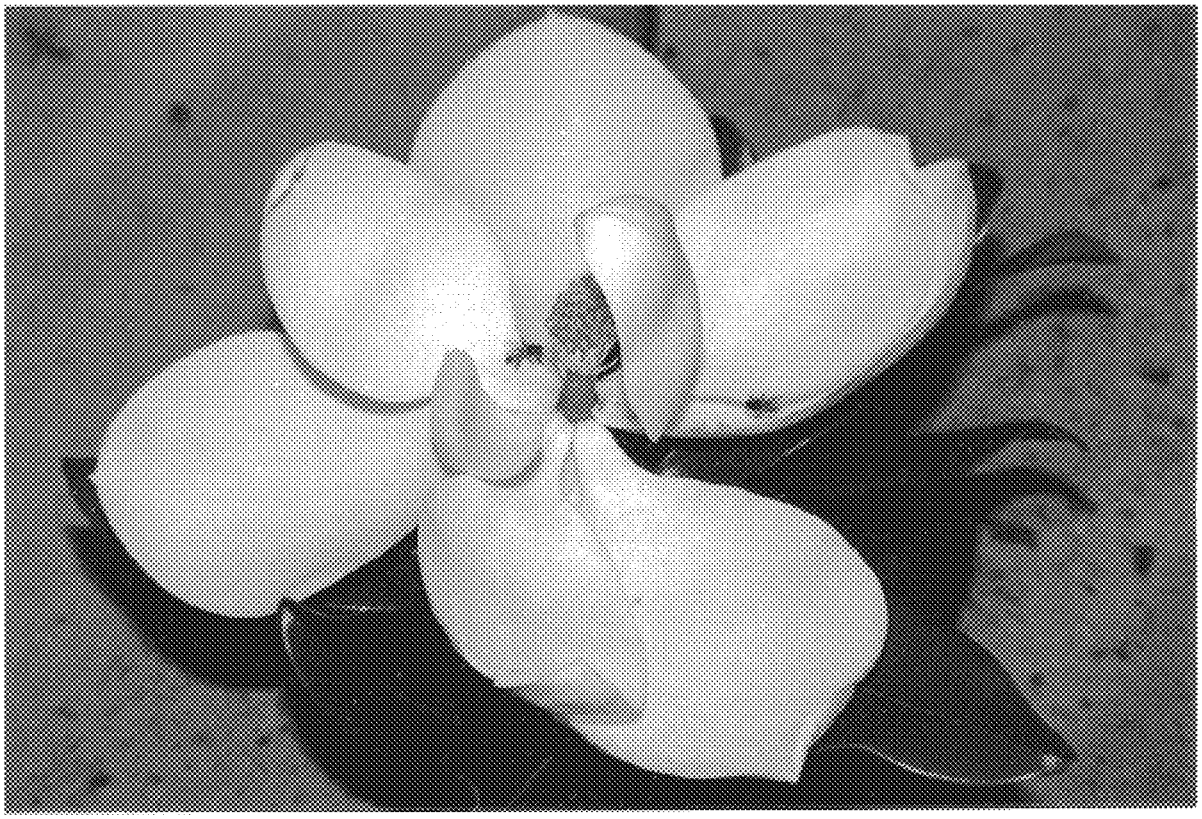
FIG. 4 illustrates a flower of the new variety.

Foliage: Alternate arranged. Thick in texture. Glossy green upper surface with pubescence on the under surface. (See FIG. 3).

*Size.*—When fully expanded is 7–9 inches long by 3–4 inches wide, more strap shape than other typical seedling varieties.

*Shape.*—Mature leaves are narrowly elliptical.

*Apex.*—Acute.

*Base.*—Cuneate.

*Margin.*—Entire, undulating.

*Venation.*—Pinnate with mid-rib having yellow-green (R.H.S. 151B) on the upper surface. Lower side of mid-rib protrudes out from the lower leaf surface.

*Color.*—The new unfolding leaves are covered on the under surface with copper-brown (R.H.S. 164A) pubescence and after fully expanded the pubescence turns greyed-brown (R.H.S. 199A). The upper leaf surface is lustrous dark green (R.H.S. 147A).

*Petiole.*—1" long, pubescence on upper and lower surfaces. Petiole pubescence color on unfolding leaves is greyed-orange (R.H.S. 164A) and changes to a color of grey brown (R.H.S. 199A) on fully expanded leaves.

Stems:

*Strength.*—Young stems, between one and two years old, are stout, strong and are approximately ¼ to ½ inches in diameter with new growth covered with pubescense. A distinctive circular scale scar is present at each node.

*Pith.*—Tightly chambered pith on one year old wood.

Leaf buds:

*Terminal.*—Large, one inch long when not actively expanding, slightly curved, and covered by a single ensheathing scale which has a rusty brown silky pubescence.

*Lateral.*—Smaller than terminals, about ⅜ to ½ inch long, born singly above the leaf scar, ovoid in shape with brownish pubescence.

Flowers:

*Petal color.*—White. (R.H.S. 155C).

*Petal size.*—5"–5.5" long and 3"–3.5" wide.

*Petal number.*—7.

*Petaloid size.*—4" long and 2" wide. The apex is very much cupped.

*Petaloid color.*—White (R.H.S. 155C).

*Petaloid number.*—3.

*Buds.*—Very long and pointed (lanceolate shape) with a length of 4–6 inches and width of ¾ to 1 inch. Tightly overlapping. Coloration—White (R.H.S. 155-C).

*Size.*—Solitary flowers. Larger than most Southern magnolias averaging about 10–12 inches in diameter with 10 petals that open to a cup-shaped configuration.

*Fragrance and texture.*—Heavy citrus-like scent. Definitely more fragrant than typical Southern magnolia with velvety textured petals.

*Flower cycle.*—Flowering is initiated in mid to late March and continuous into early July on a sustained basis, after which sporadic flowers occur throughout the rest of the year. It is common for my new Southern magnolia to sporadically flower during the coldest months in Groveland, Fla. This new Southern magnolia is considered a heavy bloomer, but not as heavy as the cultivar 'Little Gem' (unpatented).

*Leaf size.*—'CLTF1' leaves are 7"–9" long and 3"–4" wide, while 'Little Gem' leaves are 3.5"–5.5" long and 1.5"–2" wide.

*Leaf petiole.*—'CLTF1' leaf petioles are 1" long, while those of 'Little Gem' are ¾" long.

Tree size: Ultimate height of both cultivars is unknown. The expected height of 'CLTF1' is 50'–70', while the expected height of 'Little Gem' is 25'–45'.

Flower characteristics:

*Flower size.*—'CLTF1' flowers are 10"–12" in diameter, while 'Little Gem' flowers are much smaller at 4"–6' in diameter.

*Flowering period.*—'CLTF1' blooms 6 months out of the year, while 'Little Gem' blooms 9 months out of the year.

*Number of flowers per tree.*—'CLTF1' does not have as many flowers per plant as 'Little Gem' does. 'CLTF1' typically has 1 to 3 flowers on an 8' tall tree, while 'Little Gem' typically has 5–7 flowers on an 8' tree.

*Age when flowers observed.*—Two year old nursery grown plants growing in Groveland, Fla., have been observed to flower and produce fruits. In comparison, typical seed-grown Southern magnolia trees take five to ten years to produce flowers.

*Lastingness of bloom.*—48 hours for cut flower placed indoors; 3–4 days on the plant.

*Other characteristics of flowers.*—The most significant identification feature of my new plant is the unique magenta color red-purple (R.H.S. 61B) of the fruiting body just below the carpels where the stamens were attached (receptacle). This is best visible just after the petals have fully opened.

Fruits: The fruit is an aggregate of follicles that are ovoid in shape and borne singly at the end of the branch, more pubescent than typical Southern magnolia and each averaging about 3–4 inches long and 2–2½ inches wide. The fruits turn magenta in color in early August and remain colorful into November; the seeds are oval in shape and are ¼ to ⅜ inch long covered with a red aril. They naturally dehisce from the follicles in October–December and are attached by a string-like funicular stalk.

Reproductive organs:

*Stamens.*—The abaxial side (back) of the stamen is smooth, while the adaxial (front) side has parallel ridges (anthers) running from tip to base. There are multiple rows of stamens surrounding the carpels. The filaments are not thread like. They are linear in length and uniform in width (1/16"–1/8") from tip to base.

*Pistil.*—Styles are tightly bound to the carpel. They are short, flat, and come to a point at the tip with broad base where attached to the carpels. The ovaries are enclosed within the carpel.

I claim:

1. A new and distinct variety of Southern Magnolia tree as herein described and illustrated, primarily characterized by the dominant central leader with strong branching angles, a dense well branched canopy, copper-brown pubescence on the leaves and large fragrant flowers that exhibit a unique magenta color on the fruiting body.

* * * * *